United States Patent [19]

Braquet et al.

[11] Patent Number: 5,906,993
[45] Date of Patent: May 25, 1999

[54] TREATING DISORDERS CHARACTERIZED BY EXCESSIVE CELL PROLIFERATION WITH SCLAREOLIDE

[75] Inventors: Pierre Braquet, Garches; Denis Bigg, Gif-sur-Yvette, both of France

[73] Assignee: Societe de Conseils de Recherches et d'Applications Scientifiques, France

[21] Appl. No.: 08/875,476

[22] PCT Filed: Jan. 4, 1996

[86] PCT No.: PCT/FR96/00015

§ 371 Date: Sep. 17, 1997

§ 102(e) Date: Sep. 17, 1997

[87] PCT Pub. No.: WO96/20704

PCT Pub. Date: Jul. 11, 1996

[30] Foreign Application Priority Data

Jan. 4, 1995 [GB] United Kingdom .................. 9500024

[51] Int. Cl.$^6$ .................................................... A61K 31/335
[52] U.S. Cl. ............................................................ 514/468
[58] Field of Search ............................................... 514/468

[56] References Cited

PUBLICATIONS

Okamoto et al, "Inhibition of . . . Related Compounds", Cancer Letters, vol. 21, No. 1, 1983, pp. 29–35.

*Primary Examiner*—Jerome D. Goldberg
*Attorney, Agent, or Firm*—Bierman, Muserlian and Lucas

[57] ABSTRACT

A method for treating a disorder characterized by excessive cell proliferation in a patient by administering to the patient a therapeutically effective amount of sclareolide.

16 Claims, No Drawings

TREATING DISORDERS CHARACTERIZED BY EXCESSIVE CELL PROLIFERATION WITH SCLAREOLIDE (+) Sclareolide [3aR-(3aα, 5aβ, 9aα, 9bα)]-decahydro-3a,6.6.9a-tetramethylnaphtho [2,1-b] furane-2(1H)-one is a natural bicyclic terpenoid which is found for example in tobacco. II. Kaneko, Agr. Biol. Chem. 35(9): 1461 (1971). (+) Sclareolide has the following structure:

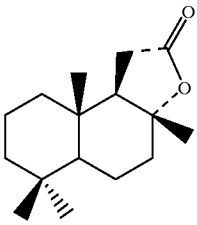

(+) Sclareolide is known for increasing or developing the organoleptic properties of food products. See for example U.S. Pat. Nos. 4,917,913; 4,960,603; 4,966,783; 4,988,527; and 4,999,207. This compound was used as a perfume for cigarettes (Japanese Patent No. 60,123,483) and as an additive to eliminate the bitter taste of coffee (U.S. Pat. No. 4,988,532).

However, to the filer's knowledge, (+) sclareolide has never been used or presented as a pharmacologically active compound.

The present invention relates to a method for inhibiting a disease characterized by excessive proliferation of cells in a patient (for example, a mammal such as man) including the administration to the patient of a therapeutically effective quantity of (+) sclareolide.

In one configuration, the patient is suffering from a disease associated with excessive proliferation of benign cells (i.e. non-malignant). Examples of such diseases are fibrosis, benign prostate hyperplasia, atherosclerosis, restenosis, glomulerosclerosis, cheloid, psoriasis, and other diseases of the skin and non-malignant neoplastic diseases.

In another configuration, the patient is suffering from a disease associated with an excessive proliferation of malignant cells (for example, cancer). Examples of such diseases are adenomas, carcinomas, cancers found in the prostate, the lungs, the liver, the pancreas, the brain, the breast, and the skin, as well as leukemia.

The therapeutically effective quantity depends upon the condition treated and the route of administration chosen, as well as the specific activity of the compound used and will be decided finally by the attending physician or veterinarian. (|) Sclareolide is administered in quantities of 0.1 to 500 mg/kg of body weight (for example, 1 to 100 mg/kg of body weight).

While it is possible to administer (+) sclareolide in the form of a pure or substantially pure compound, this product may also be presented in the form of a formula, a preparation, or a pharmaceutical composition. The formulas to be used in the present invention, both for human beings and animals, include the (+) sclareolide associated with one or more acceptable pharmaceutical vehicles of the latter and optionally other therapeutic agents. The vehicle must be "acceptable," i.e. compatible with the active ingredient(s) of the formula and not noxious to the subject to be treated.

Formulas may be conveniently presented in the form of a single dosage and may be prepared by any of the well known methods in the art of pharmacy. All methods include the phase comprising of bringing (+) sclareolide into an association with a vehicle which may contain one or more auxiliary agents. In general, compositions intended for the manufacture of tablets (for example for oral administration) or of powders are prepared by thorough and uniform mixing of (+) sclareolide with the finely divided solid vehicles, followed if necessary, as in the case of tablets, by placing the product into a mold to give it the desired size and shape.

Compositions suitable for parenteral administration (for example, subcutaneous, intravenous, or intramuscular) moreover include conveniently sterile aqueous solutions in which the (+) sclareolide is soluble. Preferably the solutions are isotonic with the blood of the subject to be treated. These compositions may be conveniently prepared by dissolving the (+) sclareolide in an aqueous solution of this type, said solution subsequently being rendered sterile. The composition may be presented in single or multiple dose containers, for example sealed vials.

Consequently the invention likewise relates to pharmaceutical compositions including as an active substance (+) sclareolide in association with one or more acceptable pharmaceutical vehicles.

Another subject matter of the invention comprises claiming the use of (+) sclareolide for the preparation of a medication intended for the treatment of diseases characterized by the excessive proliferation of cells. Examples of such diseases are fibrosis, benign prostate hyperplasia, atherosclerosis, restenosis, glomerulosclerosis, cheloid, psoriasis, and other diseases of the skin and non-malignant neoplastic diseases, adenomas, carcinomas, cancers found in the prostate, the lungs, the liver, the pancreas, the brain, the breast, and the skin, as well as leukemia.

More particularly, the invention relates to (+) sclareolide as a medication in treatment methods.

Other characteristics and advantages of the present invention will appear in the course of the detailed description of the invention and in the claims.

It is considered that a specialist may use the present invention in its entirety based upon the present description. The following specific configurations should as a result be interpreted as purely illustrative and not limiting the rest of the disclosure, regardless of its nature.

Unless they are otherwise defined, all of the technical and scientific terms used here have the same meaning as that currently understood by a person of ordinary competence in that field of technology of which this invention is a part. Likewise, all publications, patent applications, and other references cited herein are incorporated by reference.

(+) Sclareolide (+) Sclareolide is available from a specific number of commercial sources, for example Aldrich Chemical Co., St. Louis, Mo. (+) Sclareolide may likewise be prepared by synthesis, for example from (−) sclareol (Aldrich Chemical Co.) or homophamesylic acid. See for example Coste Maniere et al., Tetrahedron Letters, 29(9):1017 (1988), Mantres et al., Tetrahedron Letters 34(4):629 (1993); German Patents No. DE 4,301,555 and DE 3,942,358 and PCT Application No. WO 93/21,174.

Inhibition of the proliferation of benign prostate hyperplasia (HPB)

The solutions of (+) sclareolide are prepared by dilution with dimethylsulfoxide (DMSO) (0.5%). The culture medium used was a minimum essential medium (MEM, Gibco, Taisley, United Kingdom) without any serum but to which L-glutamine (0.6 mg/ml, Gibco), gentamycin (40 µg/ml, Gibco), penicillin (100 IV/ml, Gibco), and streptomycin (100 µg/ml, Gibco), has been added. Tritiated thymidine (dThd: spec. act. 48 Ci/mmole) was obtained from Amersham (Little Chalfont, United Kingdom). The solutions to be added to the incubation medium were prepared at the time of use by appropriate dilution with the MEM. The HPB tissue was obtained from 10 patients (age range 56–80 years; average age+/−standard deviation: 68+/−12) having prostates not previously treated, which had undergone an open tetropubic prostatectomy. The specimens were received fresh from the operating room in the MFM kept at 4° C. for 1–3 hours before being treated for organ culture as presented in detail in Y. Launoit et al., The Prostate, 13:143 (1988). For each HPB specimen, each experimental condition was determined by means of a series of 10 samples of tissue (0.5–1 mm$^3$) placed in a petri dish (3 cm in diameter, Gibco) containing 2.5 ml of MEM medium. These cultures were incubated in a control medium or in a medium to which had been added either 10 nM of Epithelial Growth Factor (FCE) or 10 nM of basic Fibroblast Growth Factor (FCFb) with or without $10^4$ M (final concentration) of (+) sclareolide. FCE or FCFb were added at the beginning of the culture. The (+) sclareolide was added 24 hours after the FCE or the FCFb. The cultures were immersed in the fixer EFA (96° ethanol, 70% by volume, neutral lormol, 25% by volume, acetic acid, 5% by volume) at the 72nd hour after the beginning of the culture, i.e. at the 48th hour after the addition of the (|) sclareolide Tritiated thymidine (2 μCi/ml MEM) was added to the culture medium four times, namely at 36 hours, 24 hours, 12 hours and 1 hour before fixation.

The method of tagging with tritiated thymidine made it possible to estimate the tagging indexes with thymidine (IMT). The IMT represents the percentage of cells involved in the S phase of the cell cycle. This index therefore represents an indirect estimate of the rate of proliferation in a given tissue. The methodology used here is identical to that presented in detail in Y. Launoit et al., The Prostate, 13: 143 (1988). The IMT was determined as follows. Two sections of each specimen were cut of the HPB. The IMT was determined separately in the stromal and epithelial compartments of each HPB. For this purpose, the IMT counts were carried out on 300–800 stromal cells and 300–800 epithelial cells per section of HPB. Thus, in sum, 600–1,600 stromal cells and 600–1,600 epithelial cells were counted per specimen of HPB and in sum, 6,000–16,000 stromal cells and 6,000–16,000 epithelial cells were counted per experimental condition. The nuclear tagging was considered positive when a node was covered by a number of grains of silver whose average value was 10 times higher than that of the background.

It was noted that the (+) sclareolide inhibited the proliferation of organotypical cells of HPB simulated by the FCFb at 70% and inhibited the proliferation of cells of HPB stimulated by the Epithelial Growth Factor at 60% for a concentration of $10^4$ M.

Inhibition of the proliferation of fibroblasts

A confluent culture of mouse embryo cells (CFS) was used to determine the proliferation of fibroblasts by measuring the incorporation of [$^3$H] methyl thymidine into the DNA of these cells. The CES were brought into suspension in a Dulbecco modified essential medium (DMEM: Gibco). The DMEM in this test comprised 1 g/l of glucose, 100 μg/ml of penicillin, 100 μg/ml of streptomycin, and 10% of fetal calf serum. 24 cavity culture plates were filled with 500 μl of the suspension (70,000 cells/cavity) and maintained for 24 hours in an incubator at 37° C. at 5% $CO_2$.

The next day, the culture medium in each cavity was replaced by 500 μl of DMEM containing 0.5% fetal calf serum for the purpose of reducing the rate of reproduction and keeping the cells in a stationary phase. The next day the culture medium was replaced (1 μl for each cavity) and the cells were stimulated with FCFb with or without a solution of varying concentrations of (+) sclareolide. The solutions of (+) sclareolide were prepared by aqueous dilution with DMSO. The next day [$^3$H] methyl thymidine (1 μCi/ml) was added and the culture plates were kept for four hours at 37° C. The incubation medium was subsequently removed and 1 ml of cooled 10% trichloracetic acid was added (ATC, Sigma Chemical). 30 minutes later at 4° C. the ATC was removed, the culture plates were rinsed with water and 500 μl of 0.3 m NaOH were added to each cavity. The culture plates were kept at 4° C. for one night. The next day the cultures of each cavity were transferred to scintillation vials. The NaOH was neutralized with 500 μl of HCl (0.3 N) and the radioactivity of the scintillation vials was measured by means of a Beckmann scintillation counter (Model No. L560000SG).

It was found that the (+) sclareolide inhibited the proliferation of fibroblasts stimulated by the FCFb 50% for a concentration of $10^{-7}$ M and 70% for a concentration of $10^{-5}$ M.

It should be understood that although the invention was presented with a detailed description, the purpose of the preceding description was to illustrate and not to limit the field of application of the invention, which is defined by the field of application of the enclosed claims. Other aspects, advantages, and modifications are given in the claims.

We claim:

1. A method of treating excessive proliferation of benign and malignant cells sensitive to the compound below in mammals comprising administering to mammals in need thereof of an amount of (+) sclareolide sufficient to reduce proliferation of benign and malignant cells.

2. A method according to claim 1, characterized in that said proliferation of cells is benign.

3. A method according to claim 2, characterized in that said (+) sclareolide is administered by parenteral route.

4. A method according to claim 2, characterized in that said (+) sclareolide is administered by subcutaneous route.

5. A method according to claim 2, characterized in that said (+) sclareolide is administered orally.

6. A method according to claim 1, characterized in that said disease is fibrosis.

7. A method according to claim 6, characterized in that said (+) sclareolide is administered by parenteral route.

8. A method according to claim 6, characterized in that said (+) sclareolide is administered by subcutaneous route.

9. A method according to claim 6, characterized in that said (|) sclareolide is administered orally.

10. A method according to claim 1, characterized in that said disease is a benign prostate hyperplasia.

11. A method according to claim 10, characterized in that said (+) sclareolide is administered by parenteral route.

12. A method according to claim 10, characterized in that said (+) sclareolide is administered by subcutaneous route.

13. A method according to claim 10, characterized in that said (+) sclareolide is administered orally.

14. A method according to claim 1, characterized in that said (+) sclareolide is administered by parenteral route.

15. A method according to claim 1, characterized in that said (+) sclareolide is administered by subcutaneous route.

16. A method according to claim 1, characterized in that said (+) sclareolide is administered orally.

* * * * *